United States Patent [19]

Takada et al.

[11] 4,406,544

[45] Sep. 27, 1983

[54] METHOD AND APPARATUS FOR MEASURING HUMAN BODY OR THE LIKE

[75] Inventors: Munekazu Takada, Uji; Toshio Esaki, Amagasaki, both of Japan

[73] Assignee: Unitika, Ltd., Japan

[21] Appl. No.: 234,781

[22] Filed: Feb. 17, 1981

[30] Foreign Application Priority Data

Feb. 19, 1980 [JP] Japan .................. 55-19924

[51] Int. Cl.$^3$ .................. G01B 11/24; G02B 27/17
[52] U.S. Cl. .................. 356/376; 250/224; 250/578; 356/387
[58] Field of Search .............. 356/376, 379, 380, 375, 356/386–387; 250/558, 224, 578

[56] References Cited

U.S. PATENT DOCUMENTS

| | | | |
|---|---|---|---|
| 3,158,744 | 11/1964 | Bernstein | 250/224 |
| 3,437,022 | 4/1969 | Hamonds, Jr. | 356/376 |
| 4,053,773 | 10/1977 | Deresh et al. | 250/578 |
| 4,192,613 | 3/1980 | Hammer | 356/386 |
| 4,297,034 | 10/1981 | Ito et al. | 356/376 |

FOREIGN PATENT DOCUMENTS

| | | | |
|---|---|---|---|
| 2729576 | 1/1979 | Fed. Rep. of Germany | 356/376 |
| 54-104163 | 8/1979 | Japan . | |
| 54-123969 | 9/1979 | Japan | 356/376 |

OTHER PUBLICATIONS

Hercher, M "An Optical System for the Automated Inspection of Diesel Engines" Proc. Conf. Soc. of Photo-Optical Instrum. Engineers, 22–23, Jan. 1979, pp. 68–72.
Sato et al., "Measurement of Polyhedral Objects by Motion Stereo", Trans. IECE of Japan, vol. E61, #8, Abstracts, 8/78, pp. 680–681.
Appel et al., "Estimating Projected Area", IBM Tech. Disc. Bull., 3/73, pp. 3234–3235.
Williams, E. R., "Two-Dimensional Image Sensor Using One-Dimensional Sensor Array", IBM Tech. Disc. Bull., 7/78, pp. 436–437.
Seemuller, W. W., "Area Measurement Using Random Image Perturbation with Discrete Arrays", IEEE Trans. on Instrum. & Meas., 5/72, pp. 140–144.
Industrial Technology supplied by Research Development Corporation of Japan in 1979, (p. 55).

Primary Examiner—William H. Punter
Attorney, Agent, or Firm—Barnes, Kisselle, Raisch, Choate, Whittemore & Hulbert

[57] ABSTRACT

An apparatus for measuring the size of the whole or a specified portion of a human body or like body comprises at least one light projecting means for projecting rays, light receiving means opposed to the light projecting means for receiving rays therefrom to detect an actual-size silhouette pattern of the body, a floor portion provided between the light projecting means and the light receiving means for positioning the body thereon, and a rotary member for rotating the two means around the body relative thereto intermittently through a small angle at a time while holding the two means opposed to each other. Measurements of the body can be taken by the apparatus automatically, rapidly and with the desired accuracy without permitting direct contact of any measuring element with the body.

16 Claims, 4 Drawing Figures

METHOD AND APPARATUS FOR MEASURING HUMAN BODY OR THE LIKE

This invention relates to a method and an apparatus for measuring the size of a human body or the like, and more particularly to a method and an apparatus for measuring the size of the whole or a specific portion of the body to be measured, the projecting rays on the body and detecting the actual-size silhouette pattern of the body.

Three-dimensional measurements of the human body have heretofore been taken by various methods, which are divided generally into two types: manual measuring methods and mechanical measuring methods. With the former methods which have long been practiced, the person to be measured is made to stand or seated still, and the measurer (with his assistant, if needed) taken three-dimensional measurements of the human body with a simple instrument, such as Martin-type measuring instrument, tape measure, ruller or angle measuring instrument, held in contact with the body. Such a method is widely used and has the great advantage that the size of any part of the body can be measured three-dimensionally as desired in detail. However, the method requires great skill and takes too long a time which causes the person to be measured to feel tedious or uncomfortable. The method therefore involves the serious drawback that the desired measurements are not always available.

The mechanical measuring methods for the human body include the sliding gauge method, silhouette method, moire method, etc. The sliding gauge method employs a multiplicity of parallel sliding bars which are arranged perpendicular to a reference plane. These bars are brought into contact with the surface of the human body at their forward ends, and the distances of the ends from the reference plane are detected and then analyzed with use of a three-dimensional orthogonal coordinate system to obtain measurements. Although suitable for dimensionally measuring local curved portions of the human body and detecting the motion of muscles, this method is not favorably acceptable because the forward ends of many sliding bars are contacted with the body.

According to the silhouette method, a silhouette of the whole human body is photographed on a reduced scale from the front or sideways to obtain measurements by re-reading. Whereas this method has the feature that the size of the body can be accurately measured two-dimensionally, the method has difficulty in taking accurate three-dimensional measurements.

The moire method, which is a photographic measuring method utilizing a moire phenomenon, affords contour intervals relating to a human body for the measurement of the size of the body. The intervals are geometrically analyzed to obtain the measurements. Although suited for detecting curved or three-dimensional shapes, this method has substantial drawbacks for wide use as a measuring method for the human body because it involves difficulties in accurately taking absolute measurements, necessitates measuring skill and requires a considerable time for the analysis.

The digitalizer method is also known for measuring the size of the human body. With this method, the surface or silhouette of the human body is scanned with a special oscillator or sensor to obtain three-dimensional or two-dimensional positions in the body, and the data obtained are analyzed by a computer to obtain three-dimensional or two-dimensional measurement. This method, as applied to the human body, is useful for taking measurements of special portions or as an auxiliary measuring method.

Thus there are various measuring methods for the human body each of which has found limited use. These methods share the same drawback that the procedure starting with measurement and ending in the calculation of the results takes some time. With some of these methods, the instrument is adapted for contact with the body to be measured but, with the exception of a very few special cases, this should absolutely be avoided in view of the psychology of the person concerned. Further the methods in which silhouettes of the human body are directly projected cause the person to feel uneasy and should therefore be avoided to the greatest possible extent.

In view of the drawbacks of the prior art described, the main object of the present invention is to provide a method and an apparatus for automatically measuring the size of the whole or a specified portion of a human body or the like within a short period of time and with the desired accuracy but without using any measuring element in direct contact with the body.

To fulfill this object, the invention provides a method of measuring the size of the whole or a specified portion of a human body or like body, comprising positioning the body in a still posture between at least one light projecting means for projecting rays and light receiving means opposed to the light projecting means, rotating the light projecting means and the light receiving means around the body relative thereto through a specified overall angle but intermittently through a small angle at a time while holding the light projecting means and the light receiving means opposed to each other, detecting an actual-size silhouette pattern of the body every time the means are rotated through the small angle to give measurements by causing the light receiving means to receive rays from the light projecting means, and analyzing the actual-size silhouette pattern as data.

The present invention also provides a measuring apparatus for practicing the foregoing method, comprising at least one light projecting means for projecting rays, light receiving means opposed to the light projecting means for receiving rays therefrom to detect an actual-size silhouette pattern of a human body or like body, a floor portion provided between the light projecting means and the light receiving means for positioning the body thereon, and a rotary member for rotating the light projecting means and the light receiving means around the body relative thereto intermittently through a small angle at a time while holding the light projecting means and the light receiving means opposed to each other.

Various features and advantages of the present invention will become more apparent from the following description of an embodiment of measuring apparatus and examples of measuring method given with reference to the accompanying drawings, in which.

Figure 1:
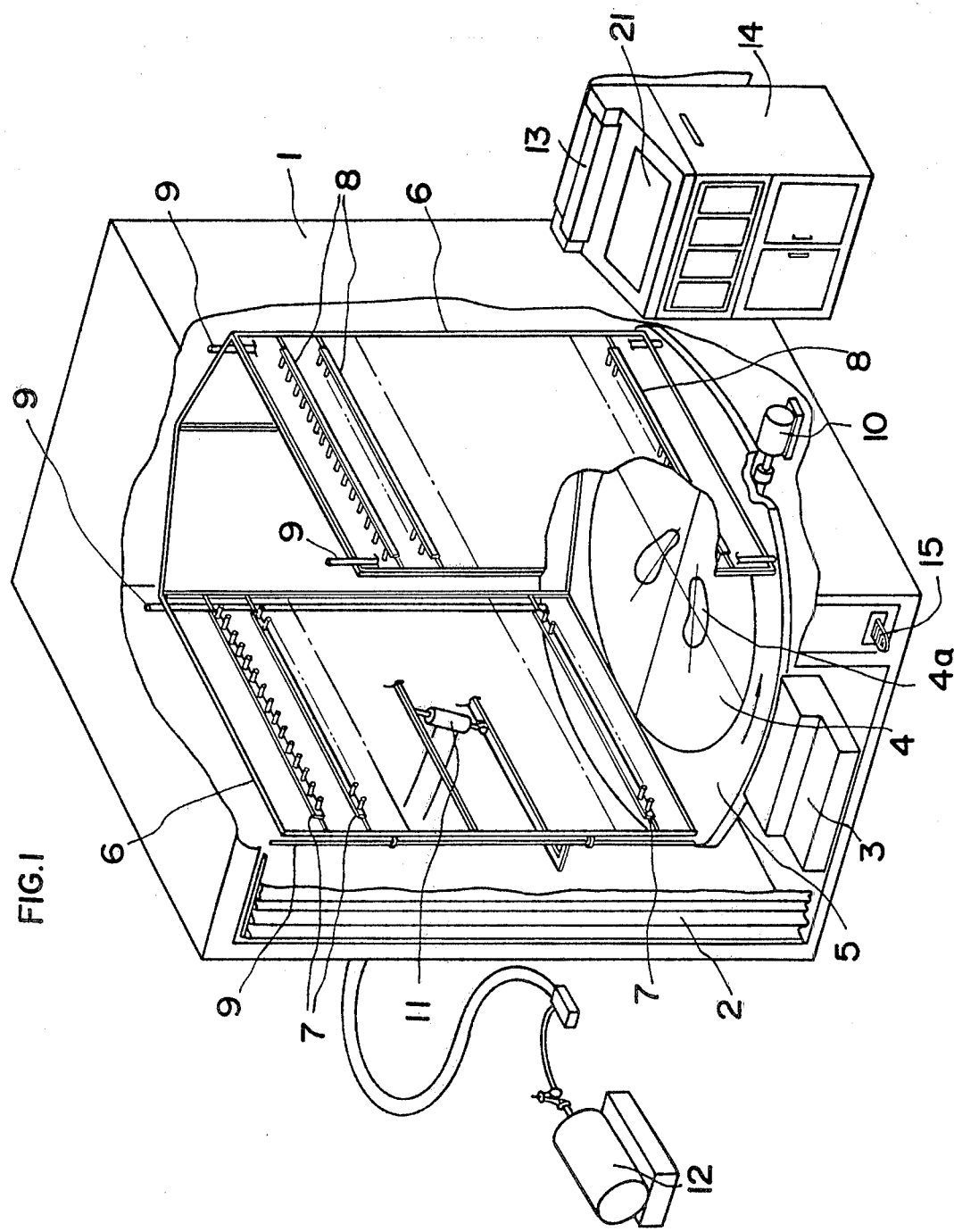
FIG. 1 is a perspective view partly broken away and showing an embodiment of the measuring apparatus of the invention.

With reference to FIG. 1 showing an embodiment of the measuring apparatus of the invention, a cabin 1 270 cm in height, 200 cm in length and 200 cm in width has a curtain 2 on the front side of the cabin. Indicated at 3 is a step member for the person to be measured. The cabin 1 is provided at the center of its lower portion with a fixed disk floor 4 about 120 cm in diameter for positioning the person thereon. The disk floor bears foot marks 4a at its center for the person to stand still thereon. The disk floor 4 is surrounded by a rotary member 5 resembling a doughnut-shaped plate and flush with the floor 4. Guide rails 9 extending upward from the rotary member 5 carry a movable frame 6 which is movable up and down along the rails 9. The rotary member 5 is slowly movable in the direction of the arrow shown. Every time the rotary member 5 rotates through an angle of 15°, the movable frame 6 moves downward and thereafter upward, such downward and upward movements each being quick and continuous. The movable frame 6 carries eight light projecting means 7 and eight light receiving means 8 to provide a light projecting plane and a light receiving plane which are parallel to each other. With the present embodiment which is adapted to take measurements for the entire body of the person to be measured, the light projecting means 7 and the light receiving means 8 are arranged vertically equidistantly at a spacing of 270 mm in the light projecting plane and the light receiving plane, respectively, to obtain actual-size silhouette patterns of the whole body. A motor 10 drives the rotary member 5 through a reduction gear. The rotary member 5 is rotated through 180° for one measuring operation, and then automatically reversely driven to the original position. Air cylinders (only one shown) 11 are coupled to a compressor 12 for quickly moving the frame 6 upward and downward to cause the light projecting means 7 and the light receiving means 8 to scan the body.

Since the movable frame 6 weighs 50 to 60 kg, the guide rails 9 are disposed at least at four locations, and the air cylinders 11 at least at two locations. Each light projecting means 7 comprises 400 separate light emitting elements, such as infrared light emitting diodes, arranged horizontally in a row at a spacing of 3 mm. Similarly each light receiving means 8 comprises 400 separate light sensing elements, such as phototransistors, arranged horizontally in a row at a spacing of 3 mm. The means 7 and 8 are moved downward by a distance of 267 mm by the air cylinder 11 to vertically scan the whole body of the person 90 times at a pitch of 3 mm during such downward movement and thereafter moved upward to their respective initial positions.

The position of rotation of the movable frame 6 rotatable with the rotary member 5, i.e. that of the means 7 and 8, is detected at an interval of 15°, for example, by the combination of a gearlike rotary disk (not shown) rotatable with the rotary member 5 and having radial projections on its outer periphery at a spacing of 15°, and a fixed photomicrosensor (not shown) which emits an electric signal every time the light incident thereon is blocked by one of the projections.

While the light projecting means 7 and the light receiving means 8 are moved downward for scanning intermittently at a pitch of 3 mm as already stated, the level of these means is detected, for example, by the combination of a racklike member (not shown) movable with the frame 6 upward and downward and having projections at a pitch of 3 mm, and a fixed photomicrosensor (not shown) which emits an electric signal when the light incident thereon is blocked by one of the projections. Such an electric signal of the photomicrosensor is also used to cause the light emitting elements of each light projecting means 7 to emit rays toward the light sensing elements of a corresponding light receiving means 8.

A computer 14 which, for example, is a microcomputer incorporating a 512K buffer memory is coupled to a typewriter 13 serving as an output unit for giving the results of measurement. Indicated at 21 is an operation panel, and at 15 a foot switch which, when depressed, initiates the present apparatus into an automatic measuring operation.

The movement of the rotary member 5, the scanning movement of the light projecting means 7 and light receiving means 8 and the feed of actual-size silhouette pattern data to the computer memory will be described with respect to timing. The rotary member 5 is started by the depression of the foot switch 15. At the same time, the means 7 and 8 are set at their upper limit position, and the computer memory is set in the initial state. When the rotary member 5 starts to rotate at a low speed for about $\frac{1}{2}$ second through a Geneva gear, the means 7 and 8 start a scanning movement. Thus every time each pair of means 7 and 8 moves downward by 3 mm, 400 digital data per pair relating to the silhouette of the person to be measured are fed to the memory of the computer 14 through an input unit (corresponding to the below-mentioned mechanical control interface). The present embodiment has eight pairs of means 7 and 8, so that the eight light receiving means 8 separately feed such sets of data to the memory to form an actual-size silhouette pattern at an angle of 0°.

When the rotary member 5 has completed its low-speed rotation for about $\frac{1}{2}$ second at 0°, that is, when the means 7 and 8 have completed the scanning movement at 0°, the rotary member 5 rotates at an increased speed and, in the meantime, the means 7 and 8 return to their upper limit position. After rotating through an angle of 15°, the rotary member 5 rotates at a low speed for about $\frac{1}{2}$ second through the Geneva gear, permitting the light projecting means 7 and the light receiving means 8 to scan the body in the same manner as above, with the result that the eight light receiving means 8 individually feed to the memory of the computer 14 digital data relating to a silhouette of the body, whereby an actual-size silhouette pattern is formed at the angle of rotation of 15°. The same procedure as above is thereafter similarly repeated at 30°, 45°, . . . 180° to form actual-size silhouette pattern at these angles.

A further description will be given of the procedure for measuring the size of the human body by the apparatus described above.

Figure 3A:
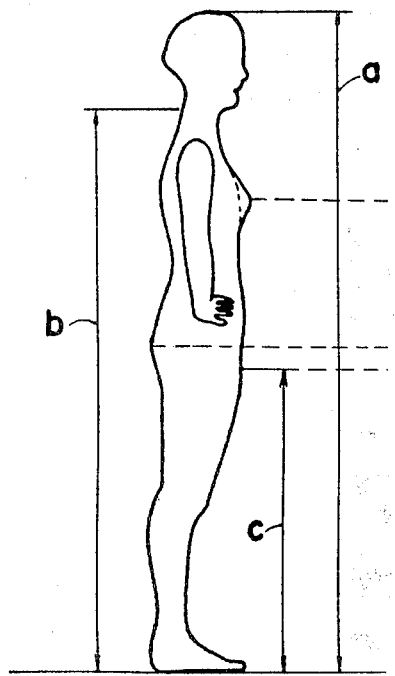
FIGS. 3a and 3b are diagrams showing a human body to illustrate the portions to be measured for exemplary purposes.
Figure 3B:
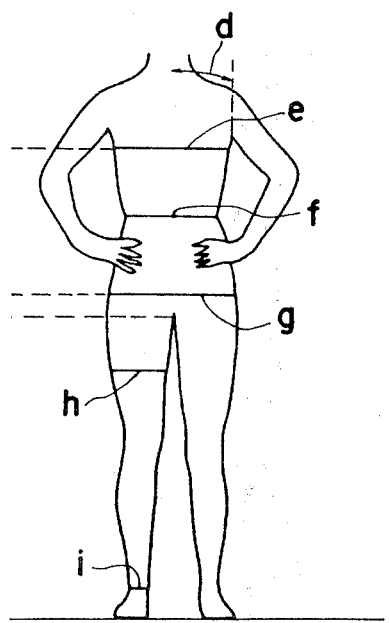

The person to be measured first opens the curtain 2, ascends the step member 3, enters the cabin 1, stands on the fixed disk floor 4 with her soles fitted to the foot marks 4a, and holds her hands to the waist with her elbows bent. Thus the person stands still as seen in FIGS. 3a and 3b. In this case, the elbows should project outward as bent at a right angle.

The person is thereafter requested to stand still in this posture for a specified period of time, for example, 13 to 25 seconds. When the measurer subsequently depresses the start switch, namely the foot switch 15, of the measuring apparatus, the doughnut-shaped rotary member 5 rotates in the direction of the arrow. Every time the rotary member 5 rotates by 15°, each pair of the light projecting means 7 and the light receiving means 8 moves downward and upward for scanning and return, whereby her actual-size silhouette patterns as converted to electric signals are automatically fed to the memory of the computer 14 as binary-digit data.

When the rotary member 5 has turned through 180°, the member 5 automatically stops and automatically reversely rotates quickly to the initial position, whereupon the member 5 stops. The person then walks out from the apparatus. During the operation described, 13 actual-size silhouette patterns of the whole body of the person, taken first from the front, then at an angular interval of 15° and finally from the rear, are collected in the computer memory.

Each light projecting means 7 having 400 light emitting elements horizontally arranged at a spacing of 3 mm projects 400 rays at a time toward a corresponding light receiving means 8 having similarly arranged 400 light receiving elements to produce 400 data. Such data production of each pair of means 7 and 8 is effected very time the pair move downward by a small distance of 3 mm and a total of 90 times while the pair move downward by a specified overall distance (267 mm). In other words, the receiving elements receive rays from the emitting elements every 3 mm during such downward movement. Thus rays are emitted once in the 0 position, once again at the 3 mm position, once again at the 6 mm position, etc., so that rays are emitted a total of 90 times during a downward movement of 267 mm. Consequently an actual-size silhouette pattern of the whole body of the person to be measured is projected on a plane with picture elements which are arranged at a spacing of 3 mm both horizontally and vertically. The pattern is fed to the memory of the computer in terms of electric digital data comprising "0" and "1", either of which is given depending on whether or not the optical paths between the light emitting elements and the light sensing elements are blocked. With the present invention, "0" represents the silhouette portion.

On completion of the actual-size silhouette patterns, the computer is operated to calculate the measurements of the desired portion of the body. Prior to the calculation, the computer compares the actual-size front silhouette pattern (angle of rotation: 0°) of the body with the actual-size rear silhouette pattern (angle of rotation: 180°) thereof to detect, within a permissible range, whether or not the person to be measured retained the specified posture. If she is found to have remained in shape, the computer analyzes the 12 patterns other than the above-mentioned rear pattern according to an automatic program to calculate the measurements of the desired portion. For example, the computer calculates the measurements of linear length between two points, circumferential length and curvature of a curved surface, and also performs calculations for drawing sectional shapes of the human body. When the circumference of a portion including a recess is to be measured, the measurement is calculated as corrected to the shortest peripheral length, as when the measurement is taken with a tape measure. The measurements thus calculated are typewritten, and the sectional shape determined is displayed. The time needed for such calculation, although dependent on the number of the measurements to be taken, is usually several minutes.

Figure 2:
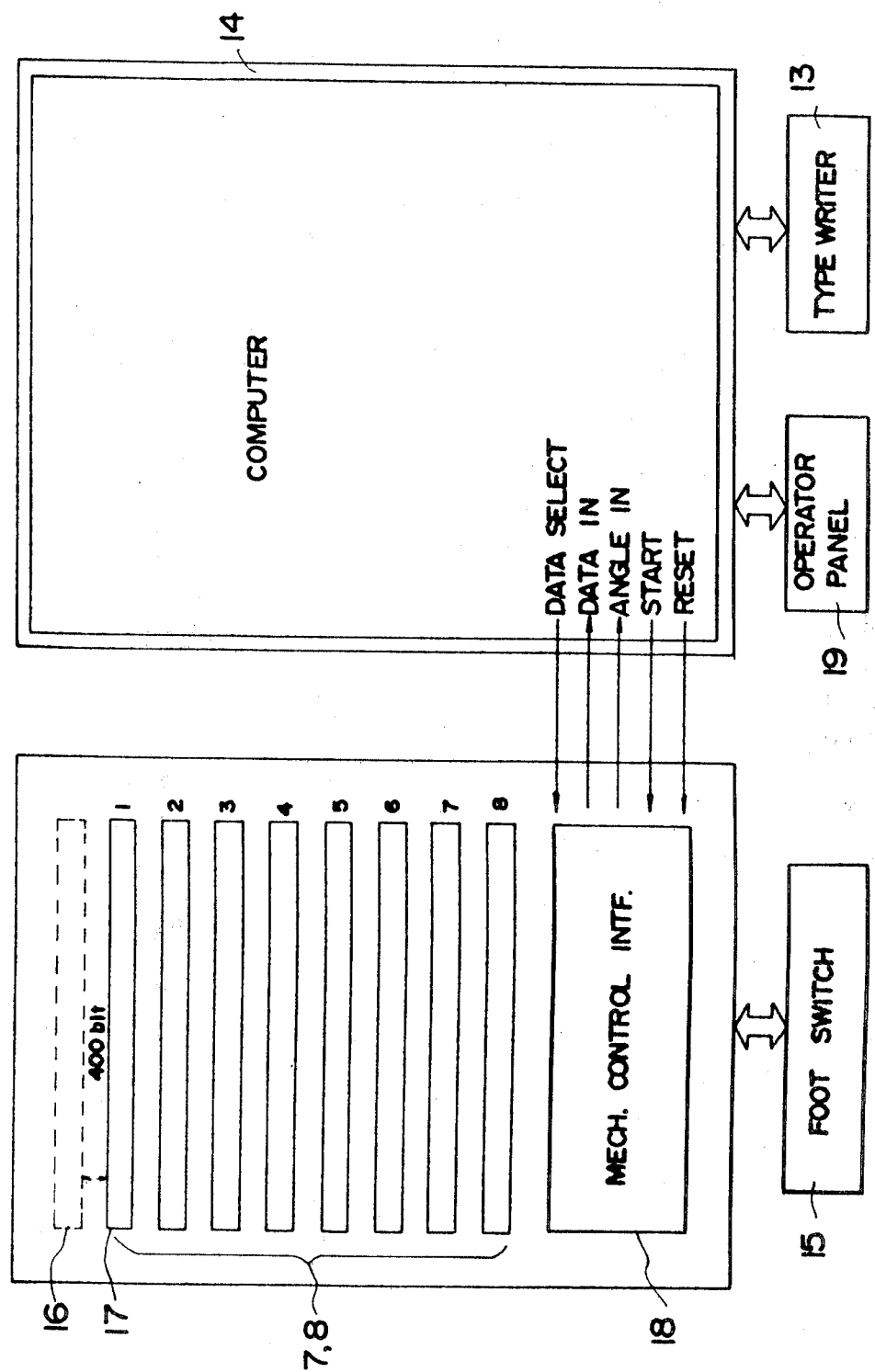
FIG. 2 is a system diagram of the embodiment.

With reference to FIG. 2 showing the system diagram of the measuring apparatus of FIG. 1, each pair of the light projecting means 7 and light receiving means 8 reciprocates between a position 16 and a position 17 (shown for the uppermost pair) every time the rotary member is rotated through 15° for the scanning and return movements already described in connection with FIG. 1. The present apparatus is automatically initiated into operation by the foot switch 15. The actual-size silhouette patterns obtained by the means 7 and 8 are fed to and stored in the buffer memory of the computer 14 in terms of digital data, along with the data of angles of rotation. These data are selectively transferred between the computer 14 and the sensor drive circuit, namely the mechanical control interface 18 for control purposes. The patterns stored in the buffer memory are automatically analyzed in response to an instruction given by an operation panel 19, and the measurements are calculated according to the procedure specified by a 28K P-ROM (programmable read-only memory) included in the computer 14. The results are given by the typewriter 13 or display (not shown). When the actual-size silhouette patterns have been taken at all the angular positions, that is, when the rotary member 5 has completely turned 180°, the member 5 returns quickly to the 0° position in response to a reset signal from the computer. The mechanical control interface 18 may be installed in any location, for example, on the movable frame 7 or the ceiling or sidewall of the cabin 1, provided that the lead wires from the interface 18 will not interfere with the rotation of the rotary portion.

For taking measurements of the human body by the present apparatus, the person is requested to stand still, for example, for ten-odd seconds in a naked state with panties on while holding the ankles spaced apart by about 30 cm and the hands placed on the waist with the elbows bent. Actual-size silhouette patterns of the person are then taken at equal angular intervals over the angle of rotation of 0° to 180° about the person. The measurements of portions of the body are calculated from the patterns. For the measurement of a certain body portion, the silhouette spectrum of that body portion will overlap that of another body portion, depending on the angular position concerned, consequently producing a lack of data. The term silhouette spectrum refers to the location and width of the silhouette portion in a certain line or column included in the plane of picture elements (plane containing an assembly of picture elements) at the angular position concerned.

Such a lack of data leads to an objection in especially in measuring circumferential or peripheral lengths. Our intensive research, however, has revealed that the objection can be eliminated by accurately estimating the lacking measurements by a special data interpolation method. Table 1 shows the angular positions where data are absent when various body regions are measured for circumferential or peripheral lengths every 15-degree angle of rotation.

TABLE 1

| Region | Regions of lack of circumferential measurements Angle (deg) | | | | | | | | | | | |
|---|---|---|---|---|---|---|---|---|---|---|---|---|
| | 0 | 15 | 30 | 45 | 60 | 75 | 90 | 105 | 120 | 135 | 150 | 165 |
| Neck | 0 | 0 | 0 | 0 | 0 | 0 | 0 | 0 | 0 | 0 | 0 | 0 |
| Shoulder | 0 | 0 | 0 | 0 | 0 | 0 | 0 | 0 | 0 | 0 | 0 | 0 |
| Above elbow | 0 | 0 | 0 | — | — | — | — | — | — | 0 | 0 | 0 |

TABLE 1-continued

| | Regions of lack of circumferential measurements | | | | | | | | | | | |
|---|---|---|---|---|---|---|---|---|---|---|---|---|
| | Angle (deg) | | | | | | | | | | | |
| Region | 0 | 15 | 30 | 45 | 60 | 75 | 90 | 105 | 120 | 135 | 150 | 165 |
| Elbow | 0 | 0 | 0 | 0 | — | — | — | — | 0 | 0 | 0 | 0 |
| Below elbow | 0 | 0 | 0 | — | — | — | — | — | — | 0 | 0 | 0 |
| Chest | 0 | 0 | 0 | — | — | — | 0 | — | — | 0 | 0 | 0 |
| Abdomen | 0 | 0 | 0 | 0 | — | — | 0 | — | — | 0 | 0 | 0 |
| Waist | 0 | 0 | 0 | 0 | 0 | 0 | 0 | 0 | 0 | 0 | 0 | 0 |
| Belt | 0 | 0 | 0 | 0 | 0 | 0 | 0 | 0 | 0 | 0 | 0 | 0 |
| Hips | 0 | 0 | 0 | 0 | 0 | 0 | 0 | 0 | 0 | 0 | 0 | 0 |
| Mid-thigh | 0 | 0 | 0 | 0 | — | — | 0 | — | — | 0 | 0 | 0 |
| Above knee | 0 | 0 | 0 | 0 | — | — | 0 | — | — | 0 | 0 | 0 |
| Knee | 0 | 0 | 0 | 0 | — | — | 0 | — | — | 0 | 0 | 0 |
| Calf | 0 | 0 | 0 | 0 | — | — | 0 | — | — | 0 | 0 | 0 |
| Ankle | 0 | 0 | 0 | 0 | — | — | 0 | — | — | 0 | 0 | 0 |

In Table 1, the mark "0" indicates the measurement available, and the mark "-" indicates the measurement which must be estimated. The absent measurement can be estimated by the linear approximation method or polynomial approximation method. Either method is used depending on the region to be measured.

When the human body size is to be measured according to this invention, the person should be positioned between the light projecting means 7 and the light receiving means 8 in a still posture. To take measurements for the whole body, the person should preferably assume an upstanding still posture. For taking measurements of the upper half only of the body, the body should preferably be in a seated posture; the person is then less likely to disturb the posture during measurement. In this case, a stool or like chair having no back is used to avoid the trouble that would otherwise be encountered in taking silhouette patterns.

For taking actual-size silhouette patterns according to this invention, the light projecting means 7 and light receiving means 8 are rotated about the person to be measured relative thereto to project rays on the person. The axis of rotation is a vertical line through the center of the person. This axis can of course be a vertical line deviating from the center of the person.

To rotate the means 7 and 8 relative to the person, these means are driven with the person positioned on the fixed floor 4 as is the case with the illustrated embodiment. Alternatively, the person may be rotated with the means 7 and 8 fixed. In the latter case, the floor is driven and serves also as a rotary member. The former arrangement is preferable since the person is less likely to disturb the still posture.

The light projecting plane of the means 7 and the light receiving plane of the means 8 are so arranged that the rays from the means 7 can be received by the means 8 on a plane perpendicular to the direction of projection of the rays. For example, these planes are disposed in parallel. The light projecting plane may be oblique or curved insofar as the light receiving plane of the means 8 is perpendicular to the direction of projection of the rays from the means 7. The means 7 and 8 are spaced apart by such a distance that the intervening person to be measured will not contact these means.

Examples of useful light emitting elements are those emitting continuous rays, such as light emitting diodes for emitting visible, ultraviolet or infrared rays, and elements for emitting laser rays. These rays are harmless to the human body and will not disturb the psychology of the person to be measured. Examples of useful light sensing elements are phototransistor, photodiode, etc. These light sensing elements function to convert light to an electric signal, that is, to a voltage, or to a voltage and then to a current.

The optical elements of each light projecting means 7 as well as of each light receiving means 8 may not necessarily be spaced apart horizontally by 3 mm as described hereinbefore, but may be optionally spaced apart within a range of 2 to 10 mm. In the same way, each optical means 7 or 8 may be adapted to intermittently project or receive rays not necessarily at a spacing of 3 mm but optionally at a spacing of 2 to 10 mm during the overall downward scanning movement thereof although the distance of such an overall scanning movement and the vertical spacing between each two vertically adjacent optical means 7 or 8 must naturally be varied from the aforementioned values of 267 mm and 270 mm respectively depending on the scanning spacing chosen. The rotary member 5 is rotated intermittently through a small angle of usually 3° to 45° at a time. Such small angele of rotation is determined in accordance with the accuracy of measurement desired.

The speed of rotation of the rotary member, that is, the speed of rotation of the means 7 and 8, is about 0.5 to 10 r.p.m. During measurement, the person to be measured should retain a still posture for about 5 to 30 seconds. This period varies with the construction of the apparatus.

The time required for the analysis of data, although varying with the number of measurements taken, is exceedingly shorter than heretofore needed since the analysis is conducted automatically by a computer. Usually the data can be processed within several minutes.

According to this invention, it is preferable that at least the means 7 and 8, floor 4 and rotary member 5 be accommodated in the cabin 1. This permits the person to be measured to remain free of psychological disturbances during measurement and gives an enhanced commercial value to the measuring apparatus. The computer 14, output unit 13 or attachments such as the compressor 12 of FIG. 1 may also be housed in the cabin 1.

With the present invention, a large computer, such as a central processing unit, or a microcomputer is usable as the computer 14. In addition to the typewriter 13, a display device and others are usable as output units.

When the measuring apparatus of this invention is used as a terminal unit for an automatic sewing system in combination with a large computer, it is possible to use output units, such as a display, automatic drawing machine for dress patterns, automatic cloth cutting machine, etc. in addition to a typewriter.

Further when the present measuring apparatus is used in combination with a medium-sized computer having a large-capacity data file, it is possible to provide a data processing system for a survey of the body sizes of a group of people and health examination.

As will be apparent from the foregoing description, the term "actual-size silhouette pattern" as used in this invention refers to an actual-size graphic silhouette produced by illuminating the whole or part of the human body with a beam of parallel rays and projecting the beam onto a planar screen perpendicular to the beam and provided by a multiplicity of dots of picture elements. The pattern is fed to the computer as binary digit data. The dots of picture elements are provided by lattice dots arranged equidistantly, for example, at a spacing of 3 mm both horizontally and vertically in the case of the illustrated embodiment, in corresponding relation to the arrangement of the separate light sensing elements.

The bodies to be measured according to the invention include the human body, human figures made as of gypsum, namely, models of human bodies. Thus they include models of human bodies of life size or on a reduced scale, models of portions of the human body, such as upper or lower half of the body, head, hand, leg, etc. By measuring sizes of such models, the balance and proportion of human bodies and various portions thereof can be investigated.

As will be apparent from the foregoing description, the present invention is characterized by collecting data in actual sizes and taking actual-size silhouette patterns at every small angle of rotation, as substantially distinct from the prior art of measuring sizes of the human body. The software analysis by a computer according to the invention not only provides measurements for linear lengths and circumferential or peripheral lengths but also affords reproductions of sectional shapes of the human body in a horizontal or vertical direction. A combined analysis of such data gives any desired three-dimensional measurements of the human body.

Briefly according to the present invention, three-dimensional measurements can be taken for human bodies automatically, quickly and accurately without contacting any measuring instrument with the human body. For an automatic garment sewing system, the invention makes it possible to practice, within a short period of time, a continuous process from taking measurements through pattern making. The invention also permits efficient investigation into and classification of body types for general purposes. The present apparatus is also suited for checking minors and adults for the growth of their body sizes and is therefore useful for the maintenance of health. Thus the invention has various advantages.

The measuring method of the invention will be described with reference to the following examples in which an INTEL 8085 type microcomputer (INTEL Corp., U.S.) incorporating a 512K buffer memory was used as the computer.

EXAMPLE 1

Actual-size silhouette patterns of the whole body of a 31-year-old baseball player (male) were taken using the automatic measuring apparatus of FIG. 1. He was made to stand still for 13 seconds in a naked state with briefs on and with his soles fitted to the foot marks 4a on the fixed disk floor 4 while holding the hands to the waist with the elbows bent. In the meantime, 13 actual-size silhouette patterns were taken, first exactly from the front, then at intervals of 15-degree angle of rotation and finally exactly from the back. The patterns were automatically fed to the memory of the computer.

Before the data were analyzed by the computer, the front pattern and the back pattern as turned upside down were superposed on each other by the computer to check whether or not he retained the still posture.

The body size measurements needed for designing a garment were calculated from the silhouette pattern data according to an automatic program. Nine sizes were measured. As shown in FIG. 3, they are: standing height a, posterior full length b, clotch height c, shoulder length d, chest girth e, waist girth f, hip girth g, fenur girth h and ankle girth i.

These sizes are divide into two kinds: linear lengths such as standing height, posterior full length, clotch height and shoulder length, and peripheral or circumferential lengths of chest, waist, hips, fenur and ankle as measured horizontally.

For the determination of the linear length, two peculiar points were located in the shape of the silhouette, and the distance between the two points was determined by an analysis with the computer. The measurement accuracy was such that the errors involved were within the range of the spacing between the dots of picture elements, i.e., 3 mm.

Since the ratio of the height of the portion to be measured (such as the waist, hips or the like) from the floor to the standing height of the person is in a definite range, a peculiar point of the shape of the silhoutte was determined in this range to determine the accurate height from the floor of the portion whose circumferential length was to be measured. With respect to the lengths (widths) of the spectra of the twelve silhouette patterns at that height, let lengths $x_1, x_2, \ldots, x_{11}$ and $x_{12}$ correspond to the angular positions of $0°, 15°, \ldots, 150°$ and $165°$ on a certain line in the plane of the picture elements. The circumferential length at the given height, L, can be calculated from the following equation:

$$L = \left( \sum_{i=1}^{12} x_i/12 \right) \times \pi. \quad (1)$$

The value is the same as the measurement taken with a tape measure. The measurement accuracy was such that the error involved was within the range of the spacing between the dots of picture elements, i.e. 3 mm. Since some silhouette spectra are absent at certain angular positions, the circumferential lengths were determined with use of a suitable data interpolation method.

It is very easy for ordinary persons to stand still for about 13 seconds. However, should the person to be measured fail to retain the still posture, accurate measurements are not available with the present apparatus. Accordingly the posture must be checked quickly by some method. With the present invention, the front silhouette pattern and the rear silhouette pattern as turned upside down are superposed on each other for this purpose. We found this method useful.

EXAMPLE 2

In the same manner as in Example, twelve actual-size silhouette patterns of a life-size figure of a female were taken exactly from the front and then an angular intervals of 15°, using the apparatus of FIG. 1. The patterns were successively fed to the memory of the computer automatically.

Based on the data of these patterns, the cross section of the waist was drawn. The horizontal silhouette spectra at the respective angular positions of the waist were used for the drawing. Thus the twelve silhouette patterns provide such spectra $x_n$ (n=1, 2, 3, ..., 12). These data are represented by:

$$(\theta_n, x_n) \quad (2)$$

where n=1, 2, 3, ..., 12, and $\theta_n$ (angle of roation)=(n−1)×15°.

Since the human body is symmetrical with respect to the vertical center line, the spectra $x_n$ may be separated into right and left portions at the center of rotation of the light projecting means 7 and the light receiving means 8. With respect to one side of the center of rotation of the human body, the above data can be substituted for the data to be obtained at an angular spacing of 15° over the range of 0° to 360°. Thus the data can be expressed by:

$$(\alpha_l, P_l) \quad (3)$$

where l is 1, 2, 3, ..., 24, and $P_l$ represents the silhouette spectra on the right or left side of the center of rotation, and $\alpha_l$ (angle of rotation) is $(l-1) \times 15°$.

There is the following relation between the formulae (2) and (3).

$$x_i = P_i + P_{i+12} \quad (4)$$

where i is 1, 2, 3, ..., 12. Thus the equation (4) shows the relation between $\theta_n$ and $\alpha_l$.

For drawing the cross section of the waist, the data (3) are used in a quadratic orthogonal coordinate system (x, y). Thus, $$y \cdot \sin \alpha_l + x \cdot \cos \alpha_l = P_l \quad (5)$$

where l is 1, 2, 3, ..., 24.

When simultaneous equations are set up for the equation (5) with respect to l and l+1, the solution is the intersection of two lines for l and l+1. Such intersections are determined in succession, and the midpoints between the adjacent intersections are connected with lines, whereby the cross section can be drawn. Since some silhouette spectra are absent at certain angular positions in this case also, an appropriate data compensation method is used.

The drawing method described is usable for various regions of the human body.

What is claimed is:

1. A method of measuring the size of the whole or a specified portion of a human body or like body comprising:
   positioning the body in a still posture between at least one elongate light projecting means for simultaneously projecting parallel rays and at least one elongate light receiving means opposed to the light projecting means, said light projecting means and light receiving means having a length greater than the width of the body;
   rotating the light projecting means and the light receiving means around the body through a specified overall angle but alternately at a high speed through a smaller angle and at a lower speed through a negligible angle;
   translationally reciprocating the light projecting means and the light receiving means in a direction parallel to the axis of said rotation of these optical means in a manner such that the optical means are moved one way while they are rotating at said lower speed;
   detecting an actual-size silhouette pattern of the body by intermittently causing the light receiving means to receive rays from the light projecting means while these optical means are translationally moved one way during each lower speed rotation thereof; and
   analyzing the actual-size silhouette pattern as data by a computer.

2. A method as defined in claim 1 wherein said overall angle is 180°.

3. A method as defined in claim 1 wherein said overall angle is a multiple of said smaller angle.

4. A method as defined in claim 2 wherein said overall angle is a multiple of said smaller angle.

5. A method as defined in claim 1 wherein the rays from the or each light projecting means are produced by a plurality of separate light emitting elements arranged in a straight row at an equal spacing of 2 to 10 mm.

6. A method as defined in claim 1 wherein said light receiving means is or are caused to receive rays from said light projecting means intermittently at an equal interval of 2 to 10 mm during each one-way translational movement of these optical means.

7. A method as defined in claim 5 wherein said light receiving means is or are caused to receive rays from said light projecting means intermittently at an equal interval of 2 to 10 mm during each one-way translational movement of these optical means.

8. A method as defined in claim 1 wherein the rays from the light receiving means are visible, ultraviolet, infrared or laser rays.

9. An apparatus for measuring the size of the whole or a specified portion of a human body or like body comprising:
   at least one elongate light projecting means for simultaneously projecting parallel rays, said projecting means having a length greater than the width of the body;
   at least one elongate light receiving means opposed to the light projecting means and having substantially the same length as the light projecting means;
   a fixed floor member for positioning the body thereon in still posture;
   means for rotating the light projecting means and the light receiving means around the body through a specified overall angle but alternately at a high speed through a smaller angle and at a lower speed through a negligible angle;
   means for translationally reciprocating the light projecting means and the light receiving means in a direction parallel to the axis of said rotation of these optical means in a manner such that the optical means are moved one way while they are rotating at said lower speed, said light receiving means being caused to intermittently receive rays from the light projecting means during such one-way translational movement to produce an actual-size silhouette pattern of the body; and a computer for analyzing the actual-size silhouette pattern as data.

10. An apparatus as defined in claim 9 wherein the light projecting plane of the light projecting means and the light receiving plane of the light receiving means are arranged in parallel to each other.

11. An apparatus as defined in claim 9 wherein said rotating means comprises an annular rotary member surrounding the floor member.

12. An apparatus as defined in claim 11 wherein said light projecting means and light receiving means are mounted on a movable frame which is mounted on guide rails extending from the rotary member.

13. An apparatus as defined in claim 12 wherein said reciprocating means comprises cylinder means connected to the movable frame.

14. An apparatus as defined in claim 9 wherein the or each light projecting means comprises a plurality of separate light emitting elements arranged in a straight row at an equal spacing of 2 to 10 mm, and the or each light receiving means comprises a corresponding number of separate light sensing elements arranged in a straight row at the same spacing as the light emitting elements.

15. An apparatus as defined in claim 14 wherein there are provided a plurality of light projecting means mutually spaced apart in a vertical plane and a corresponding number of light projecting means mutually spaced apart in a vertical plane.

16. An apparatus as defined in claim 9 wherein the light projecting means, the light receiving means, the floor member, the rotating means, and the reciprocating means are housed in a cabin.

* * * * *